US010307158B2

(12) United States Patent
Wang

(10) Patent No.: US 10,307,158 B2
(45) Date of Patent: Jun. 4, 2019

(54) ARTICULATING ASSEMBLY AND SURGICAL INSTRUMENT USING THE SAME

(71) Applicant: REACH SURGICAL INC., Tianjin (CN)

(72) Inventor: Yongfeng Wang, Tianjin (CN)

(73) Assignee: REACH SURGICAL INC., Tianjin (CN)

( * ) Notice: Subject to any disclaimer, the term of this patent is extended or adjusted under 35 U.S.C. 154(b) by 390 days.

(21) Appl. No.: 15/366,453

(22) Filed: Dec. 1, 2016

(65) Prior Publication Data

US 2017/0079648 A1 Mar. 23, 2017

Related U.S. Application Data

(63) Continuation-in-part of application No. PCT/CN2015/076776, filed on Apr. 16, 2015.

(30) Foreign Application Priority Data

Jun. 27, 2014 (CN) .......................... 2014 1 0301853
Jun. 27, 2014 (CN) ...................... 2014 2 0353944 U

(51) Int. Cl.
*A61B 17/072* (2006.01)
*A61B 17/00* (2006.01)
*A61B 17/29* (2006.01)

(52) U.S. Cl.
CPC ...... *A61B 17/072* (2013.01); *A61B 17/00234* (2013.01); *A61B 17/07207* (2013.01);
(Continued)

(58) Field of Classification Search
CPC ............ A61B 17/00234; A61B 17/072; A61B 17/07207; A61B 2017/00398; A61B 2017/2927
(Continued)

(56) References Cited

U.S. PATENT DOCUMENTS 5,954,259 A * 9/1999 Viola ............... A61B 17/07207
227/176.1
8,720,766 B2 * 5/2014 Hess .................. A61B 17/0644
227/175.1
(Continued)

FOREIGN PATENT DOCUMENTS

CN 202184762 U 4/2012
CN 102665574 A 9/2012
(Continued)

OTHER PUBLICATIONS

ISR for PCT/CN2015/076776, dated Jul. 17, 2015.

*Primary Examiner* — Alexander M Valvis
*Assistant Examiner* — Valentin Neacsu
(74) *Attorney, Agent, or Firm* — Arent Fox LLP; Michael Fainberg

(57) ABSTRACT

Disclosed are an articulating assembly and a surgical instrument using the same. The articulating assembly includes a driver assembly configured to articulate an end effector of said surgical instrument, where said driver assembly includes: a screw portion rotatably mounted in a stationary handle of said surgical instrument, an axis of which is parallel to an axis of an elongated portion of said surgical instrument, wherein said screw portion is provided with at least two segments with opposite threads; two articulation plates in connection with said two thread segments, respectively, wherein a distal end of each articulation plate is in connection with said end effector of said surgical instrument; and a rotating sleeve coaxially sheathed on said screw portion so as to be in connection therewith through a gear assembly when being located at an articulation position.

20 Claims, 4 Drawing Sheets

(52) U.S. Cl.
CPC ............... *A61B 2017/00398* (2013.01); *A61B 2017/2927* (2013.01)

(58) Field of Classification Search
USPC ...................................................... 227/176.1
See application file for complete search history.

(56) References Cited

U.S. PATENT DOCUMENTS

| | | | | |
|---|---|---|---|---|
| 8,961,542 B2* | 2/2015 | Whitfield | ............ | A61B 17/1285 227/176.1 |
| 2009/0289096 A1* | 11/2009 | Shelton, IV | ..... | A61B 17/07207 227/180.1 |
| 2009/0312773 A1* | 12/2009 | Cabrera | ............. | A61B 17/0469 606/144 |
| 2010/0320252 A1* | 12/2010 | Viola | ............... | A61B 17/07207 227/176.1 |
| 2011/0040308 A1* | 2/2011 | Cabrera | ............. | A61B 17/0469 606/144 |
| 2011/0155785 A1* | 6/2011 | Laurent | ................ | A61B 17/068 227/180.1 |
| 2012/0029533 A1* | 2/2012 | Whitfield | ............ | A61B 17/1285 606/143 |
| 2012/0029534 A1* | 2/2012 | Whitfield | ............ | A61B 17/1285 606/143 |
| 2012/0061448 A1* | 3/2012 | Zingman | ............... | A61B 17/072 227/175.2 |
| 2012/0078243 A1* | 3/2012 | Worrell | ............ | A61B 17/07207 606/33 |
| 2013/0023868 A1* | 1/2013 | Worrell | ............ | A61B 17/07207 606/33 |
| 2013/0165952 A1* | 6/2013 | Whitfield | ............ | A61B 17/1285 606/143 |
| 2013/0181030 A1* | 7/2013 | Hess | ................... | A61B 17/0644 227/175.1 |
| 2013/0274722 A1* | 10/2013 | Kostrzewski | .... | A61B 17/00234 606/1 |
| 2014/0005653 A1* | 1/2014 | Shelton, IV | ....... | A61B 18/1442 606/33 |
| 2015/0080924 A1* | 3/2015 | Stulen | ............ | A61B 17/320092 606/169 |

FOREIGN PATENT DOCUMENTS

| | | |
|---|---|---|
| CN | 103169518 A | 6/2013 |
| CN | 203970439 U | 12/2014 |
| EP | 0705571 A1 | 4/1996 |

* cited by examiner

ARTICULATING ASSEMBLY AND SURGICAL INSTRUMENT USING THE SAME

This application claims priority to and is a continuation-in-part of International Application No. PCT/CN2015/076776, filed on Apr. 16, 2015, designating the United States, and claiming the priorities of Chinese Patent Application No. 201410301853.9 filed with the State Intellectual Property Office of People's Republic of China on Jun. 27, 2014, and Chinese Patent Application No. 201420353944.2 filed with the State Intellectual Property Office of People's Republic of China on Jun. 27, 2014, both of which are hereby incorporated by reference in their entireties.

FIELD

The present invention relates to the field of medical instruments and particularly to a surgical instrument, and an articulating assembly thereof.

BACKGROUND

Endoscopic and laparoscopic surgical instruments are often preferred over traditional open surgical devices since a smaller incision tends to reduce the post-operative recovery time and complications. The use of laparoscopic and endoscopic surgical procedures has been relatively popular and has provided additional incentive to develop the procedures further. In laparoscopic procedures, surgery is performed in the interior of the abdomen through a small incision. Similarly, in endoscopic procedures, surgery is performed in any hollow viscus of the body through narrow endoscopic tubes inserted through small entrance wounds in the skin.

For example, a known surgical stapling device may include a handle portion, an elongated portion and an end effector, where the handle portion includes a stationary handle configured to be held by a user, and a movable handle configured to be operated by the user; the distal end of the handle portion is connected with the end effector through the elongated portion; and the end effector is configured to be controlled by the handle portion for simultaneously making a longitudinal incision in tissue and applies lines of staples on opposing sides of the incision to cut and suture tissue.

Positioning of an end effector may be further facilitated through inclusion of one or more articulation joints or features, enabling the end effector to be selectively articulated or rotated relative to the longitudinal axis of the shaft.

SUMMARY

The present disclosure provides a surgical instrument, and an articulating assembly thereof, where the articulating assembly can improve the precision and stability of manipulation by the surgical instrument to control an end effector to be bent and rotated.

In one aspect, a articulating assembly of a surgical instrument is provide according to the present disclosure, which includes a driver assembly configured to articulate an end effector of said surgical instrument, where said driver assembly includes:

a screw portion rotatablely mounted in a stationary handle of said surgical instrument, an axis of which is parallel to an axis of an elongated portion of said surgical instrument, wherein said screw portion is provided with at least two segments with opposite threads;

two articulation plates in connection with said two thread segments, respectively, wherein a distal end of each articulation plate is in connection with said end effector of said surgical instrument; and a rotating sleeve coaxially sheathed on said screw portion so as to be in connection therewith through a gear assembly when being located at an articulation position.

In another aspect, a surgical instrument is provided according to the present disclosure, where the surgical instrument includes a stationary handle, an end effector and an elongated portion, a distal end of which is in connection with said stationary handle;

wherein said surgical instrument further comprises a driver assembly configured to articulate an end effector of said surgical instrument, wherein said driver assembly comprises:

a screw portion rotatablely mounted in a stationary handle of said surgical instrument, an axis of which is parallel to an axis of an elongated portion of said surgical instrument, wherein said screw portion is provided with at least two segments with opposite threads;

two articulation plates in connection with said two thread segments, respectively, wherein a distal end of each articulation plate is in connection with said end effector of said surgical instrument; and a rotating sleeve coaxially sheathed on said screw portion so as to be in connection therewith through a gear assembly when being located at an articulation position; and each of said two articulation plates of said articulating assembly is connected with a proximal end of said end effector, respectively; one of said articulation plates is connected with said end effector on one side of the axis of said elongated portion, whereas the other articulation plate is connected with said end effector on the other side of the axis of said elongated portion.

Figure 1:
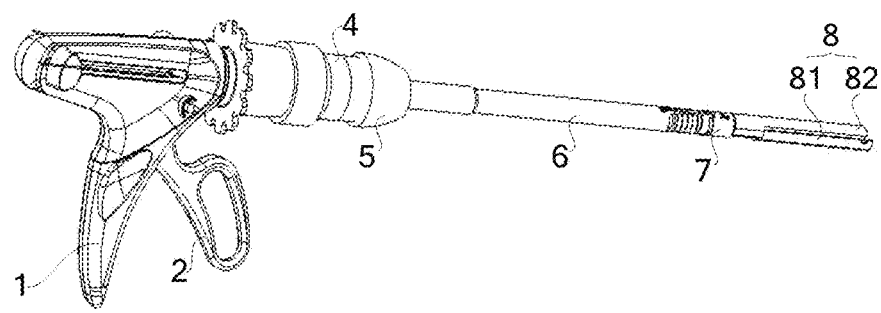
FIG. 1 is a schematic structural diagram of a surgical instrument according to an embodiment of the present disclosure.

Reference numerals:

1-stationary handle
2-movable handle
3-snap ring
301-elastic snap arm
3011-block
4-rotating sleeve
401-snap ring groove
5-casing member
6-elongated portion
7-flexible tube
8-end effector
81-cartridge
811-protrusion
812-protrusion
82-anvil
9-screw portion
901-thread segment
902-thread segment
101-articulation plate
1011-rigid sheet
1012-protrusion
102-articulation plate
1021-rigid sheet
1022-snap hole
1023-hole
103-pin
104-pin
11-locking ring
12-gear assembly
121-transmission gear
122-driven gear
1221-hole
123-inner gear
13-retraction spring
402-stop
14-closure tube
141-flange

DETAILED DESCRIPTION OF THE EMBODIMENTS

The technical solutions according to the embodiments of the present disclosure will be described below clearly and fully with reference to the drawings in the embodiments of the present disclosure, and apparently the embodiments described below are only a part but not all of the embodiments of the present disclosure. Based upon the embodiments here of the present disclosure, all the other embodiments which can occur to those skilled in the art without any inventive effort shall fall into the scope of the present disclosure.

The present disclosure provides an articulating assembly and a surgical instrument using the same. Herein, relevant concepts of the surgical instrument of prior art are introduced so as to facilitate the description of the articulating assembly of any one of the embodiments of the present disclosure, which will not be described again in the present disclosure.

Moreover, throughout this description, the term "proximal" will refer to the portion of the instrument closest to the operator and the term "distal" will refer to the portion of the instrument furthest from the operator.

Figure 2:
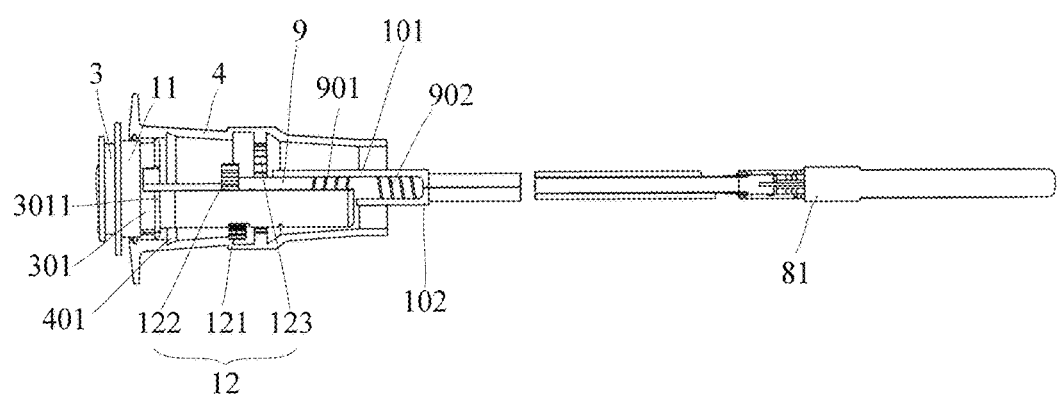
FIG. 2 is a schematic structural diagram of a articulating assembly according to an embodiment of the present disclosure.

Referring to FIG. 1 and FIG. 2, FIG. 1 shows the structure of a surgical instrument according to any one of embodiments of the present disclosure; and FIG. 2 shows the structure of an articulating assembly according to any one of embodiments of the present disclosure.

As illustrated in FIG. 1, in one embodiment of the present disclosure, the surgical instrument includes a handle portion, an elongated portion 6, and an end effector 8; the end effector 8 includes an anvil 82 and a cartridge 81; the handle portion includes a stationary handle 1 and a movable handle 2; the proximal end of the elongated portion 6 is connected with the stationary handle 1, and the distal end thereof is connected with the end effector 8 through a flexible tube 7. The surgical instrument further includes an articulating assembly configured to articulate and rotate the end effector 8 with respect to the elongated portion 6.

Preferably the surgical instrument is an endoscopic stapling device.

Figure 3:
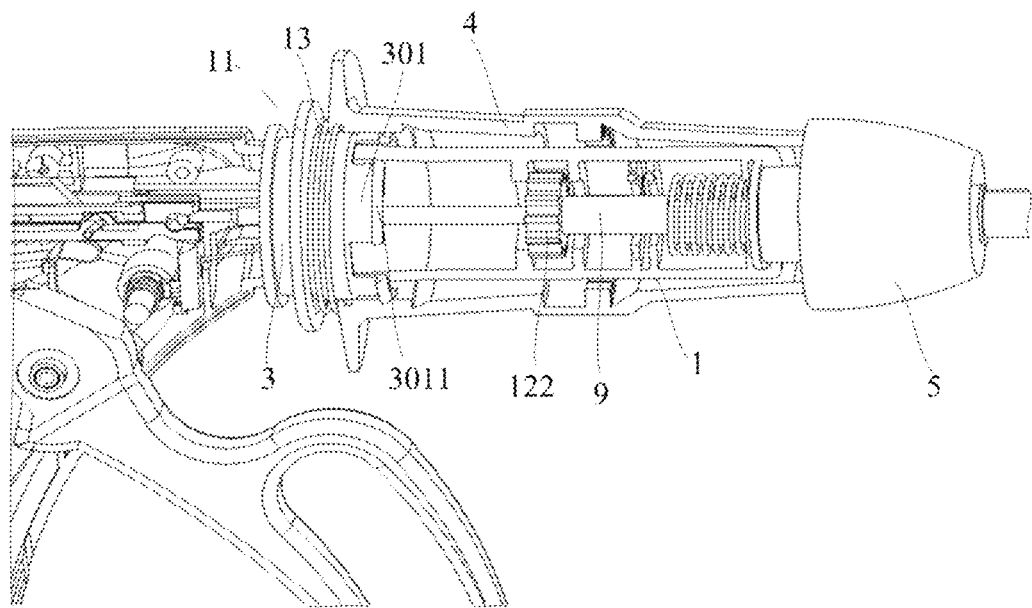
FIG. 3 is a schematic structural diagram of a driver assembly in a articulating assembly according to an embodiment of the present disclosure.

Referring to FIG. 2 and FIG. 3 together with FIG. 1, the articulating assembly of the surgical instrument according to any one of embodiments of the present disclosure includes a driver assembly configured to articulate and rotate the end effector 8 of the surgical instrument; as illustrated in FIG. 2 and FIG. 3, the driver assembly includes:

a screw portion 9 rotatably mounted on the stationary handle 1, the axis of which is parallel to the axis of the elongated portion 6, wherein, the screw portion 9 is provided with at least two segments having opposite threads. For example, in one embodiment of the present disclosure, as illustrated in FIG. 2, the segment 901 is provided with left-hand thread, whereas the segment 902 is provided with right-hand thread, and vice versa. Preferably the threads of the segments 901, 902 are external threads that are arranged around the outer surface of the screw portion 9. Of course, in an alternative embodiment of the present disclosure, the screw portion 9 can alternatively be provide with a through-hole coaxial therewith, and the two segments of threads can alternatively be arranged in the inner surface of the through-hole of the screw portion 9 (not shown).

Furthermore, the drive assembly of the articulating assembly further includes two articulation plates 101 and 102 as illustrated in FIG. 2, where the articulation plate 101 is in threaded engagement with the segment 901 of the screw portion 9, and the other articulation plate 102 is in threaded engagement with the other segment 902 of the screw portion 9.

Figure 10:
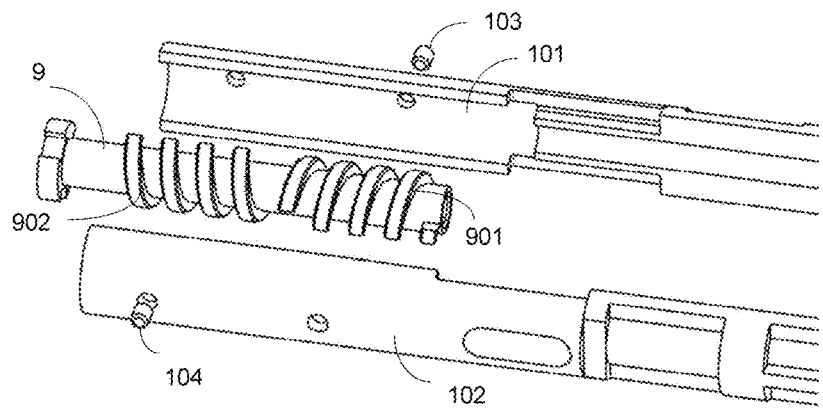
FIG. 10 is a schematic structural diagram of the connection between a screw portion and two articulation plates according to anther embodiment of the present disclosure.

In an alternative embodiment, referring to FIG. 10, the articulating plates 101 and 102 are in engagement with the two thread segments through pins 103 and 104, respectively.

Furthermore, the distal ends of the articulation plates 101 and 102 are connected respectively with the end effector 8 of the surgical instrument. More specifically, the articulation plates 101 and 102 of the articulating assembly are in connection with the proximal end of the end effector 8 on either side of the axis of the elongated portion 6, respectively. For example, as shown in FIG. 2, the articulation plate 101 is connected with the cartridge 81 of the end effector 8 on the upper side of the axis of the elongated portion 6, and the articulation plate 102 is connected with the cartridge 81 of the end effector 8 on the lower side of the axis of the elongated portion 6, so that the articulation plate 101 and the articulation plate 102 can be actuated by the screw portion 9 so as to articulate the end effector 8 with respect to the elongated portion 6.

Furthermore, in one embodiment of the present disclosure, a rotating sleeve 4 is sheathed coaxially on the screw portion 9, which can be connected with the screw portion 9 through a gear assembly when being located at an articulation position, where the end effector 8 can be articulated through rotating the rotating sleeve 4.

It should be noted that the articulation position of any one embodiment of the present disclosure refers to a position where the screw portion 9 can be rotated through rotation of the rotating sleeve 4; and a rotation position of any one embodiment of the present disclosure refers to a position where the elongated portion 6 can be rotated through rotation of the rotating sleeve 4.

The rotating sleeve 4 can be reciprocated from the rotation position to the articulation position so as to selectively enable the end effector 8 to rotate or articulate, and vice versa.

In an alternative embodiment, the rotating sleeve 4 can only be located at articulation position.

It is provided in any one of embodiments of the present disclosure the surgical instrument including the articulating assembly, wherein, the rotating sleeve 4 is in connection with the screw portion 9 through the gear assembly when being located at the articulation position, so that rotating the rotating sleeve 4 may actuate the screw portion 9 to be rotated via the gear assembly; furthermore, since the articulation plate 101 is in threaded engagement with the segment 901 of the screw portion 9, and the other articulation plate 102 is in threaded engagement with the other segment 902 of the screw portion 9, and the segments 901,902 of the screw portion 9 are provide with opposite oriented threads, thus, when the screw portion 9 rotates, for example, when the screw portion 9 rotates clockwise, the articulation plate 101 moves distally, and the other articulation plate 102 moves proximally, so as to articulate the end effector 8 rightwards with respect to the elongated portion 6, and vice versa.

When the rotating sleeve 4 is located at the articulation position, the rotating sleeve 4 and the screw portion 9 can be connected stably and force therebetween can transmitted reliably due to the gear assembly arranged therebetween and threaded engagement between the screw portion 9 and the articulation plates. Moreover, displacement of each of the articulation plates 101 and 102 can be adjusted through rotation of the screw portion 9 rotated by the rotating sleeve 4, so that the articulation angle of the end effector 8 with respect to the elongated portion can be adjusted precisely.

In addition, rotation of the rotating sleeve 4 can be stopped at any position, thus displacement of each of the two articulation plates can be adjusted as needed within a certain range, which means the angle of end effector 8 with respect to the elongated portion 6 can be adjusted consecutively within a certain range.

Figure 4:
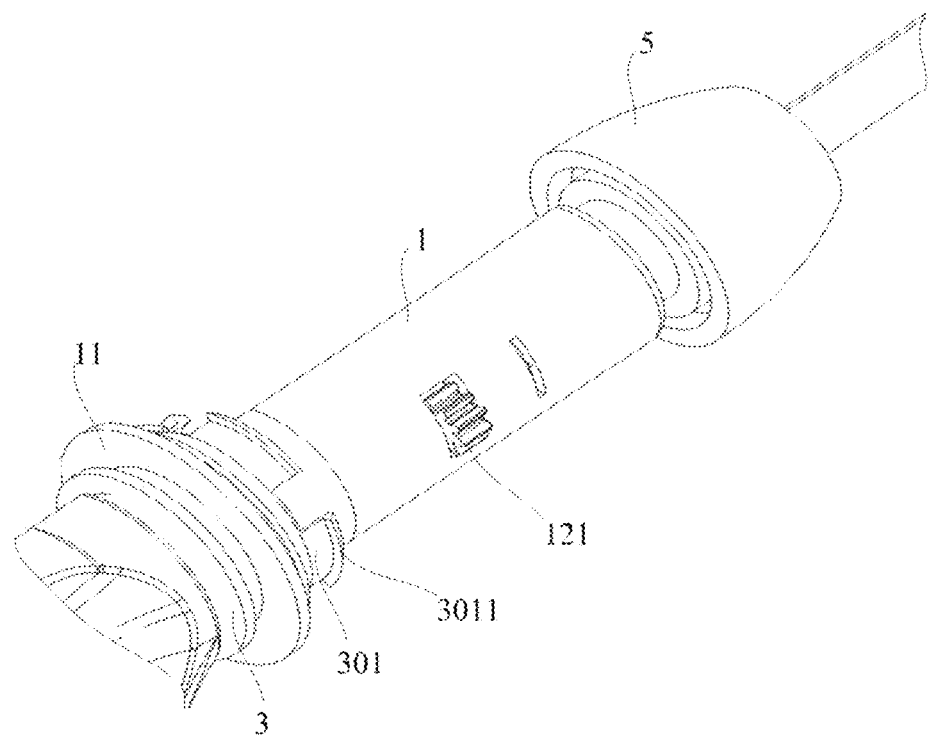
FIG. 4 is a schematic structural diagram of the connection between a transmission gear in a gear assembly of a driver assembly in a articulating assembly according to an embodiment of the present disclosure, and a stationary handle.

Referring to FIG. 2, FIG. 3, and FIG. 4, the rotating sleeve 4 is in connection with the screw portion 9 through the gear assembly when being located at the articulation position. More specifically, as illustrated in FIG. 2, internal teeth 123 are arranged on the inner surface of the rotating sleeve 4; and a driven gear 122 is fixed coaxially with the screw portion 9.

As illustrated in FIG. 2 and FIG. 4, at least one transmission gear 121 is arranged within the stationary handle 1, the axis of which is parallel to the axis of the screw portion 9, and each transmission gear 121 is engaged with both of the driven gear 122 and the internal teeth 123 on the inner surface of the rotating sleeve 4.

The rotating sleeve 4 can be reciprocated from the rotation position to the articulation position so as to selectively enable the end effector 8 to rotate or articulate, and vice versa. As illustrated in FIG. 2, for example, the rotating sleeve 4 may firstly move proximally to the articulation position, where the internal teeth 123 on the inner surface of the rotating sleeve 4 are engaged with the transmission gear 121. Therefore, the transmission gear 121 can be actuated through rotating the rotating sleeve 4. Since the transmission gear 121 is engaged with the driven gear 122, rotating the transmission gear 121 may actuate the driven gear 122 to revolve around the axis of the screw portion 9 and further to rotate the screw portion 9.

Referring to FIG. 4, in a preferred embodiment of the present disclosure, the transmission gear 121 is such mounted in the stationary handle 1 that partial teeth thereof are extended out of the stationary handle 1 through an opening thereon, so that the transmission gear 121 can be engaged with the internal teeth 123 on the inner surface of the rotating sleeve 4.

In a preferred embodiment of the present disclosure, a plurality of the transmission gears 121 are provided, which are equally spaced around the driven gear 122.

Figure 5:
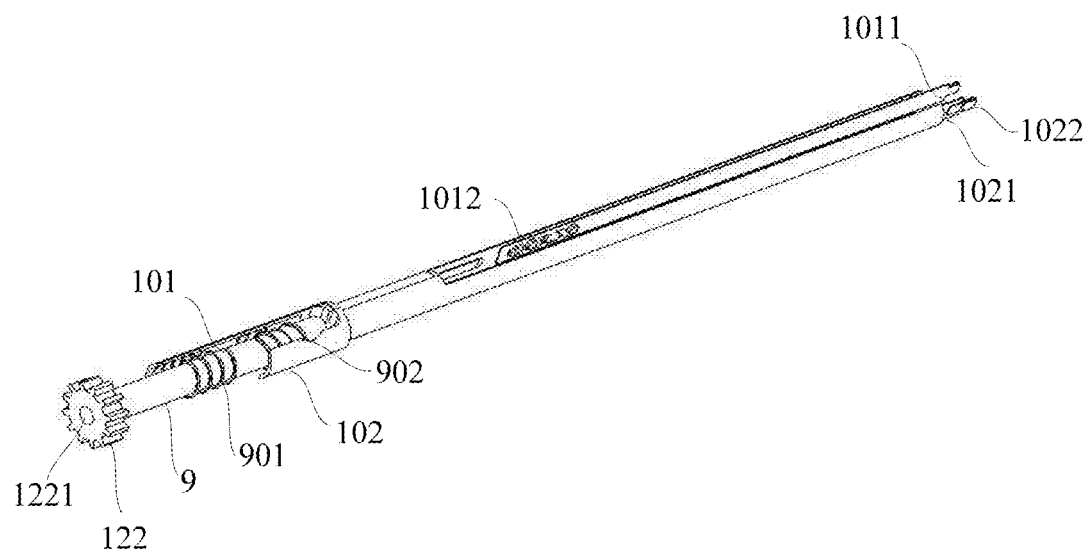
FIG. 5 is a schematic structural diagram of the connection between a screw portion and two articulation plates according to an embodiment of the present disclosure.

Furthermore, in one embodiment of the present disclosure, the movable handle of the surgical instrument is in connection with a firing mechanism having a firing rod, which is configured to close and fire the end effector 8. For facilitating the arrangement of the firing rod of the firing mechanism of the surgical instrument provided in any one of embodiments of the present disclosure, it is preferred that, as illustrated in FIG. 5, the screw portion 9 is provided with a hole 1221 coaxial therewith, through which the firing rod of the surgical instrument can pass, so as to drive the end effector 8 to perform cutting, stapling, and/or other actions.

As illustrated in FIG. 2, FIG. 3, and FIG. 4, for facilitating the rotating sleeve 4 to rotate more stably at the articulation position, the articulating assembly further includes a snap ring 3 coaxially in connection with the screw portion 9, which is axially fixed in the stationary handle 1. When the rotating sleeve 4 is located at the articulation position, the snap ring 3 is axially fixed with respect to the rotating sleeve 4 through an annular groove 401 and at least one block.

As illustrated in FIG. 2 and FIG. 3, the annular groove 401 is formed in the inner surface of the rotating sleeve 4, and the snap ring 3 is provided with the block 3011 that can be snapped into the annular groove 401.

Referring to FIG. 3 and FIG. 4, it is preferred that a plurality of elastic snap arms 301 are equally spaced around the snap ring 3, each of which is provided with a block formed on the external surface thereof, and the annular groove 401 is formed in the inner surface of the rotating sleeve 4. When the rotating sleeve 4 moves proximally, the inner surface of the rotating sleeve 4 can contact with each of the blocks 3011, respectively, so as to bias each of the elastic snap arms 301 inwards; and when the rotating sleeve 4 moves to the articulation position, each block 3011 may be pushed into and received by the annular groove 401 under the bias of the elastic snap arm 301 so as to thereby prevent the rotating sleeve 4 from moving distally with respect to the stationary handle 1.

For facilitating release of the rotating sleeve 4 from the snap ring 3, preferably as illustrated in FIG. 2 and FIG. 3, the articulating assembly further includes a locking ring 11 arranged within the rotating sleeve 4 and coaxially sheathed on the snap ring 3, which can be reciprocated with respect thereto. When moving distally, the locking ring 11 may bias each of the elastic snap arms 301 inwards that may further force each of the blocks 3011 being disengaged with the annular groove 401 of the rotating sleeve 4 to thereby release the rotating sleeve 4 from the snap ring 3.

Further referring to FIG. 3, the articulating assembly further includes a retraction spring 13 sheathed on the locking ring 11, and when the rotating sleeve 4 is located at the articulation position and the locking ring 11 moves distally, the retraction spring 13 is biased, where the proximal end of the retraction spring 13 contacts with the locking ring 11, and the distal end contacts with the rotating sleeve 4.

Accordingly, after each of the blocks 3011 of each of the corresponding elastic snap arms 301 of the snap ring 3 being disengaged from the annular groove 401 of the rotating sleeve 4, the rotating sleeve 4 can move distally under the bias of the retraction spring 13 to thereby avoid the snap blocks 3011 of the elastic snap arms 301 of the snap ring 3 from being pushed again into the annular groove 401 of the rotating sleeve 4 after being released.

In an alternative embodiment of the present disclosure, the retraction spring 13 can alternatively be mounted between the stationary handle 1 and the rotating sleeve 4. In addition, the retraction spring 13 may be arranged in various ways that will not be described in details here.

As illustrated in FIG. 3 and FIG. 4, the rotating sleeve 4 can be reciprocated from the rotation position to the articulation position so as to selectively enable the end effector 8 to rotate or articulate. In one of the embodiments of the present disclosure, the articulating assembly further includes a casing member 5 axially fixed with the housing of the elongated portion 6 of the surgical instrument, which can rotate around the axis of the elongated portion 6. In one of the embodiments of the present disclosure, the articulating assembly further includes a casing member 5 rotatably in coaxial connection with the elongated portion 6, which is further axial fixed with the housing of the elongated portion 6. When the rotating sleeve 4 is located at the rotation position, the casing member 5 is rotated together with the rotating sleeve 4 due to a circumferential limiting mechanism arranged therebetween. Thus, when the rotating sleeve 4 is located at the rotation position, the end effector 8 can be rotated through rotation of the rotating sleeve 4.

Particularly, the circumferential limiting mechanism arranged between the rotating sleeve 4 and the casing member 5 can include:

a plurality of stripped protrusions arranged on the outer surface of the rotating sleeve 4, extending along the axis of the screw portion 9; and a plurality of grooves arranged in the inner surface of the casing member 5 correspondingly, configured to receive the stripped protrusions.

In a preferred embodiment of the present disclosure, for allowing self-locking between the screw portion 9 and each of the articulation plates, the pitch of each segment of the screw portion 9 satisfies the equation of:

$P <= \pi * d * \tan(\rho)$, where:

P represents pitch of each segment; d represents pitch diameter; and $\rho$ represents an equivalent friction angle.

It is mentioned in one of embodiments of the present disclosure that the distal end of each of the articulation plates of the articulating assembly is in connection with the end effector 8.

Figure 6:
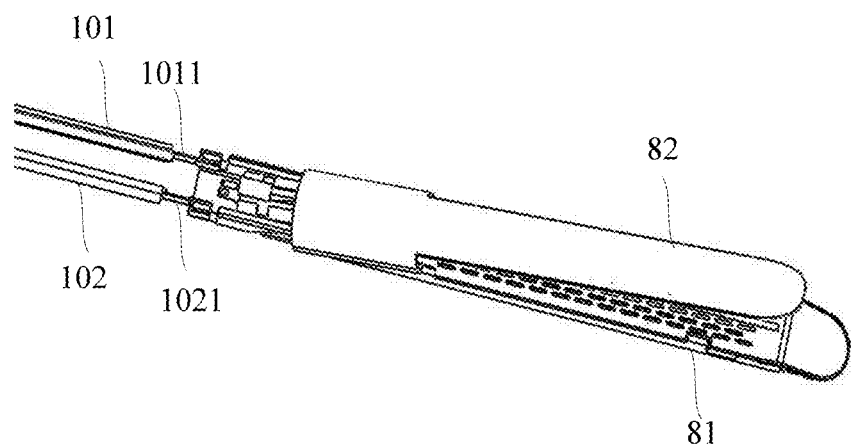
FIG. 6 is a schematic structural diagram of the connection between two articulation plates in a articulating assembly according to an embodiment of the present disclosure, and an end effector.
Figure 7:
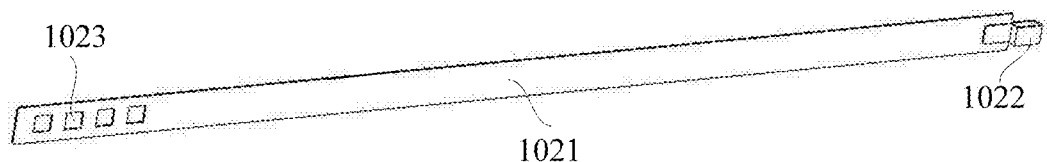
FIG. 7 is a schematic structural diagram of a rigid sheet according to an embodiment of the present disclosure.
Figure 8:
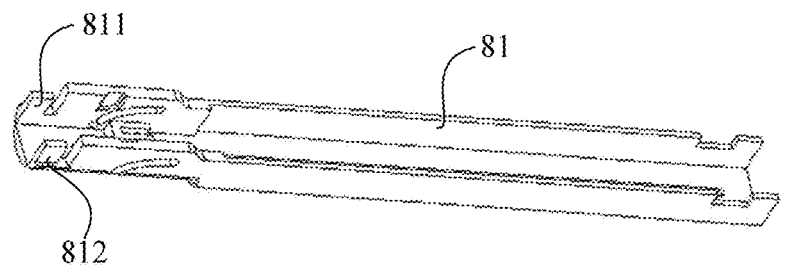
FIG. 8 is a schematic structural diagram of a cartridge cooperating with the rigid sheet structured as illustrated in FIG. 7.

More specifically, in one embodiment of the present disclosure, each articulation plate is provided with a rigid sheet, the distal end of which is provided with a connector have an opening configured to be connected with a protrusion arranged on the proximal end of the cartridge. Particularly, referring to FIG. 5 and FIG. 6, a rigid sheet 1011 in connection with the articulation plate 101 is provided with a connector having an opening for being coupled to the protrusion of the cartridge 81 of the end effector 8. As illustrated in FIG. 5, FIG. 6 and FIG. 8, the connector with the opening is arranged on the rigid sheet 1011, and the protrusion 811 is arranged on the cartridge 81. Similarly, as illustrated in FIG. 5, FIG. 6 and FIG. 7, a rigid sheet 1021 in connection with the articulation plate 102 is provided with a connector having an opening for being coupled to a protrusion of the cartridge 81 of the end effector 8. More specifically, the connector with the opening 1022 is arranged on the rigid sheet 1021, and the protrusion 812 is arranged on the cartridge 81.

Further referring to FIG. 5, the rigid sheet 1011 can be connected with the articulation plate 101 via connection between the protrusions arranged on the articulation plate 101 and the corresponding holes arranged in the rigid sheet 1011; and similarly, the rigid sheet 1012 can be connected with the articulation plate 102 via connection between the protrusions arranged on the articulation plate 102 and the corresponding holes 1023 arranged on the rigid sheet 1021, as illustrated in FIG. 8.

In an alternative embodiment of the present disclosure, each articulation plate is provided with a connector directly disposed on the distal end thereof, having an opening configured to be connected with the end effector 8 of the surgical instrument, more specifically, with two protrusions arranged on the proximal end of the cartridge 81 of the end effector 8, respectively.

Figure 9:
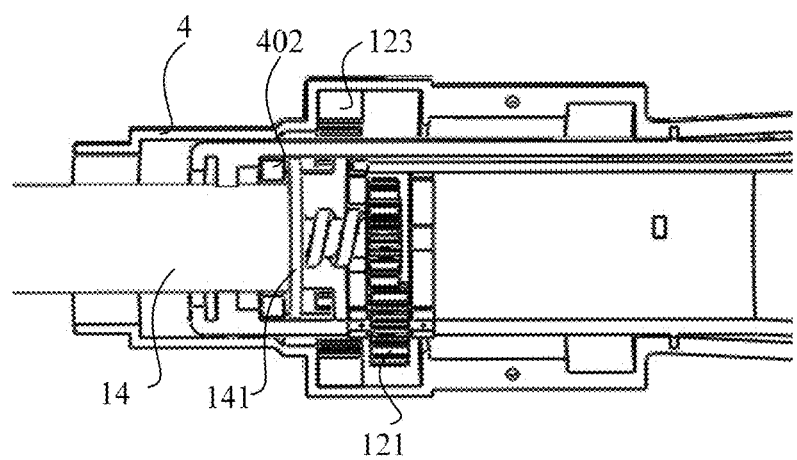
FIG. 9 is a schematic structural diagram of the cooperation between a closure tube and a rotating sleeve in a surgical instrument according to the present disclosure.

Further to any above disclosed embodiment of the present disclosure, referring to FIG. 9, the gear assembly includes the internal teeth 123, the driven gear 122, and the transmission gear 121, where the surgical instrument further includes a closure tube 14 with an axis parallel to the axis of the elongated portion 6, which can be reciprocated with respect to the stationary handle 1; a flange 141 is arranged on the proximal end of the closure tube 14, and a stop 402 is formed on the inner wall of the rotating sleeve 4. When the closure tube 14 is located at a closure position, and the rotating sleeve 4 is located at the rotation position, and the distal portion of the flange 141 of the closure tube 14 is contacted against the stop 402 of the rotating sleeve 4, which may prevent the rotating sleeve 4 from moving to the articulation position, so that the internal teeth 123 of the rotating sleeve 4 cannot be engaged with the driven gear 121, as well as the end effector of the surgical instrument cannot be articulated when it is closed, which improves the security of the surgical instrument in use.

Evidently those skilled in the art can make various modifications and variations to the present disclosure without departing from the spirit and scope of the present disclosure. Thus the present disclosure is also intended to encompass these modifications and variations thereto so long as the modifications and variations come into the scope of the claims appended to the present disclosure and their equivalents.

The invention claimed is:

1. An articulating assembly for a surgical instrument, comprising a driver assembly configured to articulate an end effector of said surgical instrument, wherein said driver assembly comprises:
   a screw portion rotatably mounted in a stationary handle of said surgical instrument, an axis of which is parallel to an axis of an elongated portion of said surgical instrument, wherein said screw portion is provided with at least two segments with opposite threads;
   two articulation plates in connection with said two segments, respectively, wherein a distal end of each articulation plate is in connection with said end effector of said surgical instrument; and
   a rotating sleeve coaxially sheathed on said screw portion so as to be in connection therewith through a gear assembly when being located at an articulation position.

2. The articulating assembly according to claim 1, wherein, said two articulation plates are in threaded engagement with said two segments, respectively.

3. The articulating assembly according to claim 1, wherein, said two articulation plates are in engagement with said two segments through pins, respectively.

4. The articulating assembly according to claim 1, wherein said gear assembly comprises:
   a plurality of internal teeth arranged on an inner surface of said rotating sleeve;
   a driven gear coaxially fixed on said screw portion; and
   at least one transmission gear rotatably arranged in said stationary handle, wherein, an axis of each transmission gear is parallel to the axis of said elongated portion, and each transmission gear is engaged with said driven gear and said internal teeth of said rotating sleeve, respectively.

5. The articulating assembly according to claim 4, wherein a plurality of transmission gears are equally spaced around said driven gear.

6. The articulating assembly according to claim 4, wherein a hole is arranged in a center of said screw portion, configured to allow a firing rod of said surgical instrument passing through.

7. The articulating assembly according to claim 1, wherein a snap ring is axially fixed in said stationary handle, as well as coaxial with said screw portion; when said rotating sleeve is located at an articulation position, said snap ring is axially fixed with respect to said rotating sleeve through an annular groove and at least one block.

8. The articulating assembly according to claim 7, wherein a plurality of elastic arms are equally spaced around the snap ring, each of which is provide with said block formed on an external surface thereof, and said annular groove is formed in an inner surface of said rotating sleeve.

9. The articulating assembly according to claim 8, wherein a locking ring is arranged within said rotating sleeve and coaxially sheathed on said snap ring, which can be reciprocated with respect to said snap ring; when said locking ring moves distally, the inner wall thereof contacts with the distal portion of each of said elastic arms so that said elastic arms are bent inwards.

10. The articulating assembly according to claim 9, further comprising a retraction spring sheathed on said locking ring, wherein when said rotating sleeve is located at the articulation position, said locking ring moves distally with respect to said snap ring so as to bias said retraction spring against said locking ring and said rotating sleeve, respectively.

11. The articulating assembly according to claim 7, further comprising a casing member in rigid connection with said elongated portion of said surgical instrument, wherein when said rotating sleeve is located at a rotation position, said casing member is non-rotatable with respect to said rotating sleeve through a circumferential limiting mechanism.

12. The articulating assembly according to claim 1, wherein pitch of each thread segment of the screw portion satisfies an equation of:

$P <= \pi*d*\tan(\rho)$, wherein:

P represents pitch of each thread segment; d represents pitch diameter; and ρ represents an equivalent friction angle.

13. The articulating assembly according to claim 1, wherein each of the articulation plates is provided with a rigid sheet in connection therewith, the distal end of which is provided with a connector having an opening adapted for being coupled to a protrusion of a cartridge.

14. The articulating assembly according to claim 13, wherein each of the rigid sheets is connected with the corresponding articulation plate through connection between a plurality of holes and protrusions.

15. The articulating assembly according to claim 1, wherein each of the articulation plates is provided with a connector having an opening arranged on the distal end thereof, adapted for being coupled to a protrusion of a cartridge.

16. A surgical instrument, comprising a stationary handle, an end effector and an elongated portion, a distal end of which is in connection with said stationary handle;
   wherein said surgical instrument further comprises a driver assembly configured to articulate an end effector of said surgical instrument, wherein said driver assembly comprises:
   a screw portion rotatably mounted in a stationary handle of said surgical instrument, an axis of which is parallel to an axis of an elongated portion of said surgical instrument, wherein said screw portion is provided with at least two segments with opposite threads;
   two articulation plates in connection with said two segments, respectively, wherein a distal end of each articulation plate is in connection with said end effector of said surgical instrument; and
   a rotating sleeve coaxially sheathed on said screw portion so as to be in connection therewith through a gear assembly when being located at an articulation position; and
   each of said two articulation plates of said articulating assembly is connected with a proximal end of said end effector, respectively; one of said articulation plates is connected with said end effector on one side of the axis of said elongated portion, whereas the other articulation plate is connected with said end effector on the other side of the axis of said elongated portion.

17. The surgical instrument according to claim 16, wherein, said two articulation plates are in threaded engagement with said two segments, respectively.

18. The surgical instrument according to claim 16, wherein, said two articulation plates are in engagement with said two segments through pins, respectively.

19. The surgical instrument according to claim 16, wherein if said gear assembly comprises internal teeth, a driven gear, and a transmission gear, then said surgical instrument further comprises a closure tube with an axis parallel to the axis of said elongated portion, and said closure tube can be reciprocated with respect to said stationary handle; and a flange is arranged on the proximal end of said closure tube, and a stop is formed on the inner wall of said rotating sleeve; when said closure tube is located at a closure position and said rotating sleeve is located at a rotation position, the distal end of said flange is contacted against said stop of said rotating sleeve.

20. The surgical instrument according to claim 19, wherein said surgical instrument is an endoscopic stapling device.

* * * * *